(12) United States Patent
Ichikawa et al.

(10) Patent No.: US 8,532,740 B2
(45) Date of Patent: Sep. 10, 2013

(54) MEASUREMENT DEVICE AND MEASUREMENT METHOD

(75) Inventors: Kazuhiro Ichikawa, Fukuoka (JP); Hideo Utsumi, Fukuoka (JP)

(73) Assignee: Kyushi University, Fukuoka (JP)

( * ) Notice: Subject to any disclaimer, the term of this patent is extended or adjusted under 35 U.S.C. 154(b) by 241 days.

(21) Appl. No.: 13/002,920

(22) PCT Filed: Jul. 7, 2009

(86) PCT No.: PCT/IB2009/006533
§ 371 (c)(1),
(2), (4) Date: Jan. 6, 2011

(87) PCT Pub. No.: WO2010/004427
PCT Pub. Date: Jan. 14, 2010

(65) Prior Publication Data
US 2011/0112395 A1    May 12, 2011

(30) Foreign Application Priority Data
Jul. 8, 2008 (JP) .................................. 2008-178217

(51) Int. Cl.
*A61B 5/05* (2006.01)

(52) U.S. Cl.
USPC .............................. 600/411; 378/196; 600/407

(58) Field of Classification Search
None
See application file for complete search history.

(56) References Cited

U.S. PATENT DOCUMENTS

| 6,302,579 | B1 | 10/2001 | Meyer et al. |
| 6,603,991 | B1 | 8/2003 | Karmalawy et al. |
| 7,190,991 | B2 | 3/2007 | Cable et al. |
| 7,412,027 | B2 | 8/2008 | Yakubovsky et al. |
| 2001/0037062 | A1* | 11/2001 | Ehnholm ................ 600/414 |
| 2005/0152492 | A1 | 7/2005 | Yakubovsky et al. |

FOREIGN PATENT DOCUMENTS

| EP | 1 593 342 A1 | 11/2005 |
| JP | 2000-157536 | 6/2000 |
| JP | 2002-143142 | 5/2002 |
| JP | 2006-075596 | 3/2006 |
| JP | 2006-204551 | 8/2006 |
| JP | 2007-316008 | 12/2007 |
| WO | WO 2006/080417 A1 | 8/2006 |

OTHER PUBLICATIONS

PCT International Search Report on application No. PCT/IB/2009/006533 dated Dec. 15, 2009; 3 pages.

(Continued)

*Primary Examiner* — Unsu Jung
*Assistant Examiner* — Saurel J Selkin
(74) *Attorney, Agent, or Firm* — Foley & Lardner LLP

(57) ABSTRACT

A measurement device and measurement method make it possible to eliminate the load generated by stopping on a measurement subject that is moved among multiple magnetic field generating devices. The measurement device includes a first external magnetic field generating device that generates a magnetic field of a set size, a second external magnetic field generating device that generates a magnetic field of a size that differs from that of the magnetic field of the first external magnetic field generating device, a rotating table that causes the subject of measurement to pass in sequence through the magnetic fields of the first and second external magnetic field generating devices by causing the subject of measurement to move rotationally, and an OMRI measurement processing part and MRI measurement processing part that measures images such as functional images or structural images of the subject of measurement while it is being moved rotationally by the rotating table.

10 Claims, 8 Drawing Sheets

(56) References Cited

OTHER PUBLICATIONS

Utsumi, Hideo, et al.; Simultaneous molecular imaging of redox reactions monitored by Overhauser-enhanced MRI with N and N-labeled nitroxyl radicals; Sep. 16, 2005; pp. 1463-1468; PNAS, vol. 103, No. 5.

Utsumi, Hideo, et al., "Molecular Imaging of in vivo Redox dynamics using Magnetic Resonance System", *Function and Materials*, vol. 28, No. 7, pp. 77-86 (2008).
Redox Life Science: State-of-Arts and Perspective; National Institute of Advanced Industrial Science & Technology, Human Stress Signal Research Center; Nov. 28, 2006; 48 pages.
Supplementary European Search Report dated Apr. 18, 2013 in EP 09794062.1, 8 pgs.

* cited by examiner

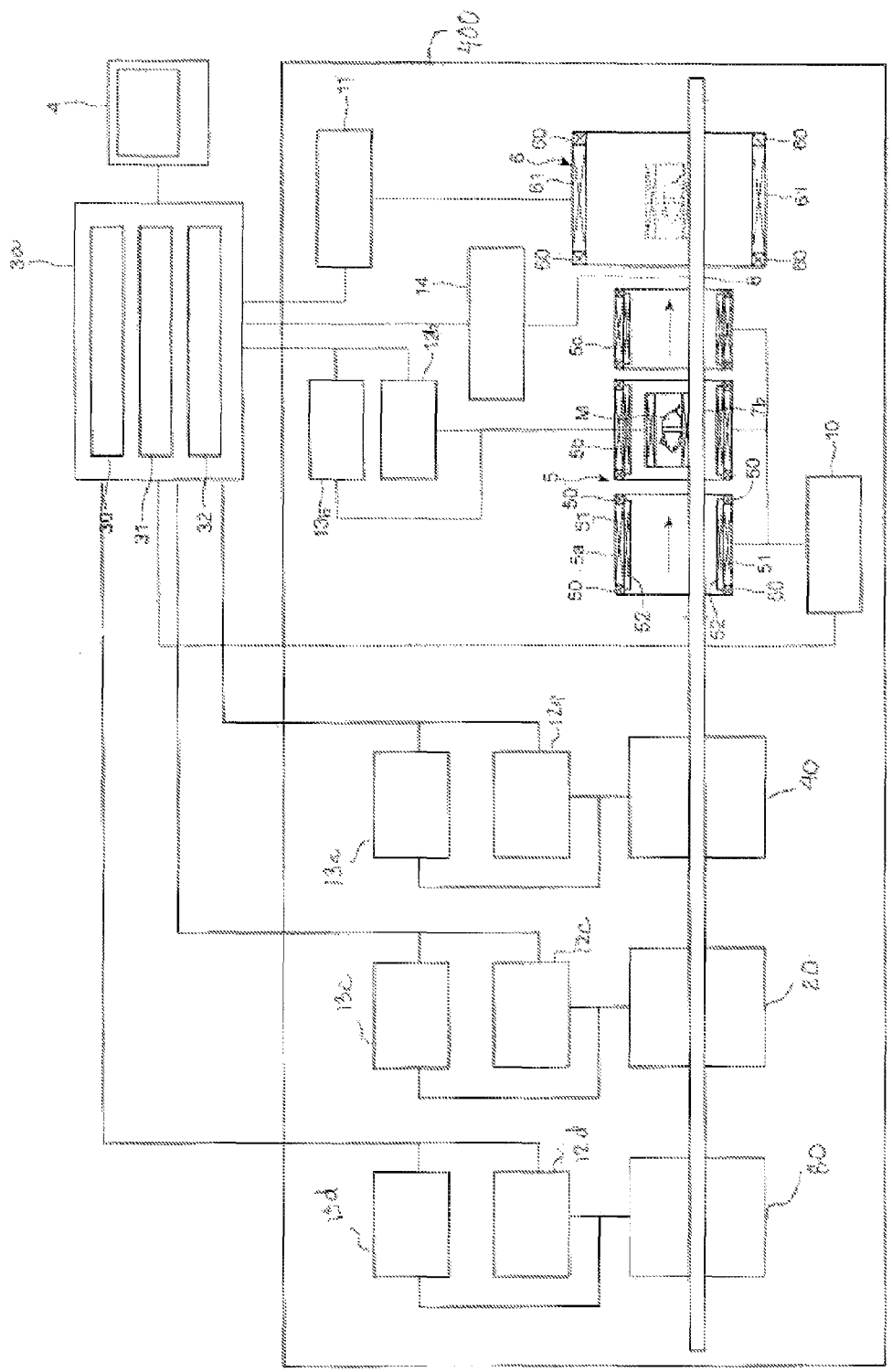

MEASUREMENT DEVICE AND MEASUREMENT METHOD

BACKGROUND OF THE INVENTION

1. Field of the Invention

The present invention relates to measurement devices and measurement methods for obtaining images, such as functional images, structural images, etc., for a measurement subject using various types of magnetic resonances, such as an electron spin resonance (ESR), nuclear magnetic resonance (NMR), etc.

2. Description of the Related Art

Redox metabolism, including active oxygen and free radicals, is closely involved in many physiological phenomena and disease components and progress. Thus, if it is possible to make redox dynamics visible at the individual level, in small experimental animals, there is no doubt that this would greatly contribute to the clarification of vital phenomena, the analysis of disease, the establishment of therapeutic methods for such diseases, and the development of drugs.

Electron spin resonance imaging (ESRI), which specifically detects free radicals, which are intermediate products of redox metabolism, is effective in making redox dynamics visible. However, ESRI images are lacking when it comes to handling internal organs. In order to solve this problem, ESRI/MRI integrated magnetic resonance image analysis devices have been developed that overlay MRI images of internal organs obtained using the nuclear magnetic resonance imaging method (MRI) on the ESRI image.

The Overhauser effect is the phenomenon of the electron spins of free radicals being made to undergo ESR transition, and nuclear spins are polarized through dipolar operation of electron spins and nuclear spins. OMRI is an imaging method wherein an MRI measurement is performed by exciting the electron spins of free radicals and then polarizing the spins of the hydrogen nuclei of water molecules. In OMRI, the nuclear spin polarization is strengthened by a maximum (theoretical value) factor of 330 relative to the normal Boltzmann distribution of nuclear spin. That is to say, it is possible to achieve a 330-fold (theoretical value) improvement in sensitivity relative to an ordinary MRI measurement.

The present applicants have proposed in Japanese Unexamined Patent Application Publication 2006-204551, a biometric device for obtaining histological images of organisms using various types of magnetic resonance, including electron spin resonance, nuclear magnetic resonance, etc. This biometric device includes a first magnetic field generation device that generates a magnetic field of a set size, a second magnetic field generation device that generates a magnetic field that is larger than the magnetic field of this first magnetic field generation device, a linear movement device that causes the organism that is the subject of measurement to move linearly between the first and second magnetic field generation devices in synchronization with the radiation of RF pulses, and a measurement processing device that stops the organism that is the subject of measurement and measures histological images of the organism that is the subject of measurement based on signals that are detected according to the RF pulses.

In this biometric device, the first magnetic field generation device can be used as an ESRI external magnetic field generation device and a PEDRI (OMRI) electron spin excitation device, and the second magnetic field generation device as an MRI and OMRI external magnetic field generation device, so that the time variable images of the radical amount can be obtained as OMRI, and the qualitative alteration images can be obtained as four-dimensional spectrum/spatial ESRI/MRI; since the magnetic field from the second magnetic field generation device can be made larger, high-sensitivity, high-resolution images can be obtained.

Incidentally, with this biometric device, the organism that is the subject of measurement is moved repetitively by the linear movement device provided between the first and second magnetic field generation devices, and measurement is performed after the organism is stopped, so large acceleration is generated when moving and stopping the organism. Thus, there is the problem that a large load is imposed on the moving organism to be measured by this biometric device.

The purpose of the present invention is to provide a measurement device and measurement method that allows the load on the organism that is the subject of measurement to be eliminated by measuring the organism that is the subject of measurement without stopping it as it moves through multiple magnetic field generation devices.

BRIEF SUMMARY OF THE INVENTION

The measurement device of the present invention includes a first magnetic field generation device that generates a magnetic field of a set size, a second magnetic field generation device that generates a magnetic field of a size that differs from that of the magnetic field of the first magnetic field generation device, a rotational movement device that causes a measurement subject to pass in sequence through the magnetic fields of the first and second magnetic field generation devices by causing the measurement subject or the first and second magnetic field generation devices to move rotationally, and a measurement device that measures images of the measurement subject in different magnetic fields without stopping it or the magnetic field generation devices while it is (they are) being moved rotationally by the rotational movement device.

Moreover, the measurement method of the present invention is characterized in that it includes causing a measurement subject to pass in sequence through the magnetic fields of a first magnetic field generation device that generates a magnetic field of a set size and a second magnetic field generation device that generates a magnetic field of a size that differs from that of the magnetic field of the first magnetic field generation device by causing the measurement subject or the first and second magnetic field generation devices to move rotationally, and measuring images of the measurement subject in different magnetic fields without stopping the measurement subject or the first and second magnetic field generation devices while it is (they are) being moved rotationally by said rotational movement device.

With these inventions, it is possible to obtain images such as functional images, histological images, etc. of the measurement subject by causing magnetic fields of differing sizes to be generated by multiple magnetic field generation devices, causing the measurement subject or the first and second magnetic field generation devices to move rotationally, and using various types of magnetic resonances such as electron spin resonance, nuclear magnetic resonance, etc. while causing the measurement subject to pass through the magnetic fields of these multiple magnetic field generation devices sequentially.

The bodies of living beings (organisms), objects other than organisms (for instance, semiconductors), etc. can be given as examples of measurement subjects for the present invention. If the measurement subject is an organism, it is possible to obtain images such as organism functional images such as redox dynamics images and metabolic images, etc. as functional images, and structural images such as histological images ($^{13}$C, $^1$H, $^{31}$P nuclei, etc.), etc. Moreover, if the measurement subject is an object, it is possible to obtain structural images of the structure, defects, etc., and distribution images of structural compounds.

In this case, for obtaining redox dynamics images, it is desirable that either the first or second magnetic field generation device is for performing measurement by exciting nuclear magnetic resonance, and that the other be for performing measurement by exciting electron spin resonance. By doing this, it is possible to obtain organism redox dynamic images through OMRI.

Either one of the first or the second magnetic field generation device may generate the larger magnetic field, but if the second magnetic field generation device generates a magnetic field larger than the magnetic field generated by the first magnetic field generation device, it is possible to use the first magnetic field generation device, with a lower magnetic field, as an OMRI electron spin excitation device, and the second magnetic field generation device, with a higher magnetic field, as an MRI and OMRI external magnetic field generation device. By doing this, MRI images and OMRI images can be obtained from the second magnetic field generation device. Specifically, with this measurement device, since OMRI measurement is performed using the second magnetic field generation device, with a high magnetic field, after electron spin is excited by the first magnetic field generation device, with a low magnetic field, the OMRI external magnetic field becomes extremely large, and it is possible to obtain high-sensitivity, high-resolution OMRI images.

On the other hand if the first magnetic field generation device generates a magnetic field that is larger than the magnetic field generated by the second magnetic field generation device, it is possible to use the first magnetic field generation device, with a higher magnetic field, as an MRI external magnetic field generation device, and to use the second magnetic field generation device, with a lower magnetic field, as an OMRI external magnetic field generation device. By doing this it is possible to obtain MRI images from the first magnetic field generation device, and to obtain OMRI images from the second magnetic field generation device.

Thus, since the measuring device of the present embodiment is intended to perform measurement through the first and second magnetic field generation devices exciting magnetic resonance, it is possible to obtain images such as functional images, structural images, etc. of the measurement subject by using various types of magnetic resonances, such as electron spin resonance, nuclear magnetic resonance, etc.

(1) Since the structure is such that the measurement subject is made to pass through the magnetic fields of the first and second magnetic field generation devices sequentially, and images of the measurement subject are measured in different magnetic fields without stopping the measurement subject or the first and second magnetic field generation devices, there is no need to cause the measurement subject to move repetitively, and it is possible to obtain functional and structural images of the measurement subject by using various types of magnetic resonances such as electron spin resonance, nuclear magnetic resonance, etc. while causing the measurement subject or the first and second magnetic field generation devices to move rotationally without stopping, therefore, there being no stopping for measurement as with conventional devices, it is possible to eliminate the load generated by stopping. Moreover, there is also no load imposed on the first and second magnetic field generation devices by stopping.

(2) By having either the first or the second magnetic field generation device be for exciting nuclear magnetic resonance, and the other for exciting electron spin resonance, it is possible to obtain organism redox dynamics images using OMRI.

(3) If the magnetic field generated by the second magnetic field generation device is larger than the magnetic field generated by the first magnetic field generation device, since it is possible to use the first magnetic field generation device, with a low magnetic field, as an OMRI electron spin excitation device, and to use the second magnetic field generation device as an MRI and OMRI external magnetic field generation device, the OMRI external magnetic field becomes extremely large, and it is possible to obtain high-sensitivity, high-resolution OMRI images.

(4) If the magnetic field generated by the first magnetic field generation device is larger than the magnetic field generated by the second magnetic field generation device, since it is possible to use the first magnetic field generation device, with a high magnetic field, as an MRI external field generation device, and to use the second magnetic field generation device, with a low magnetic field, as and OMRI external magnetic generation device, it is possible to obtain high-sensitivity OMRI images.

BRIEF DESCRIPTION OF THE DRAWINGS

FIG. 9 is an outline framework of a measurement system according to another embodiment of the present invention.

DETAILED DESCRIPTION OF THE INVENTION

Figure 1:
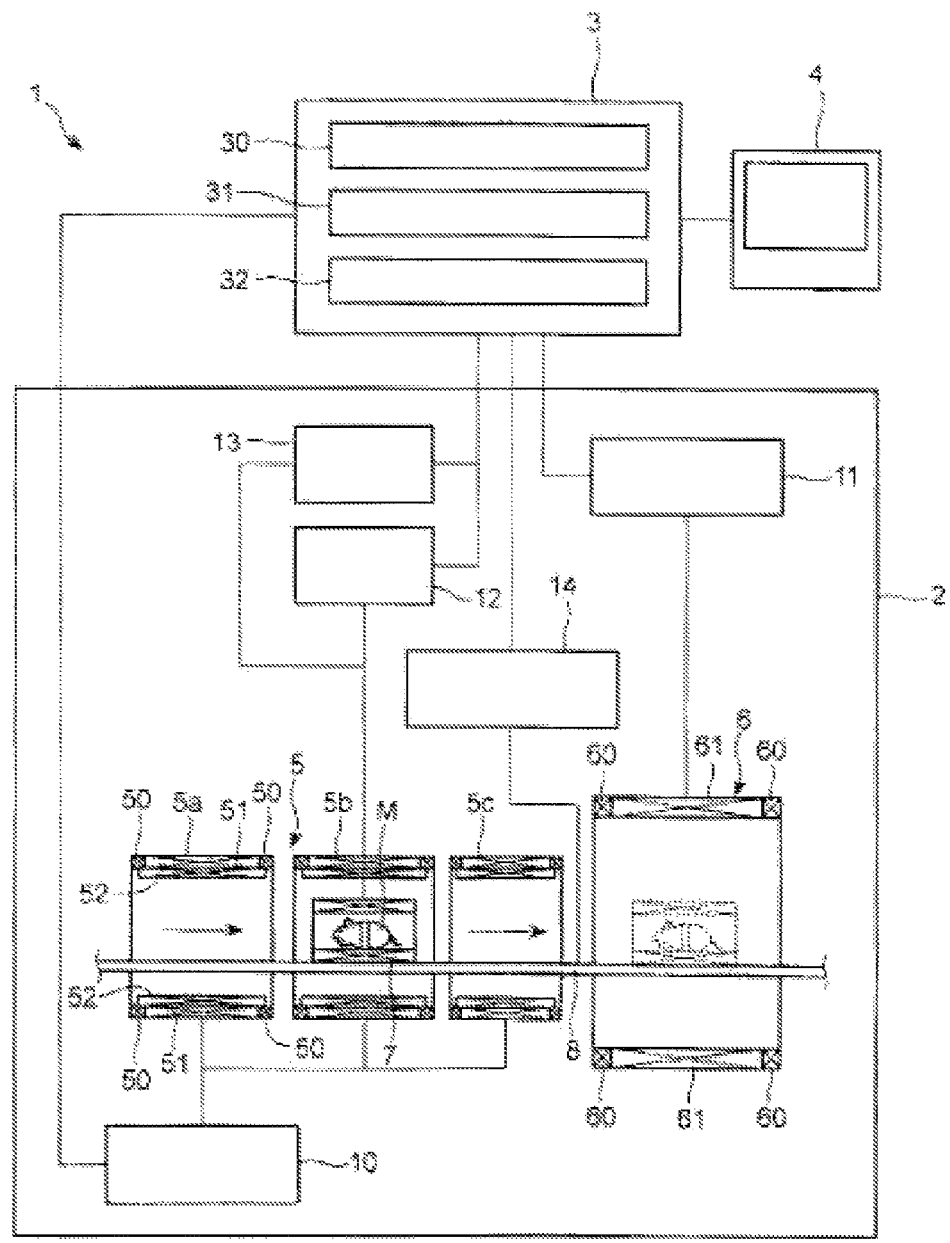
FIG. 1 is a outline framework of a measurement device according to a first embodiment of the present invention.
Figure 2:
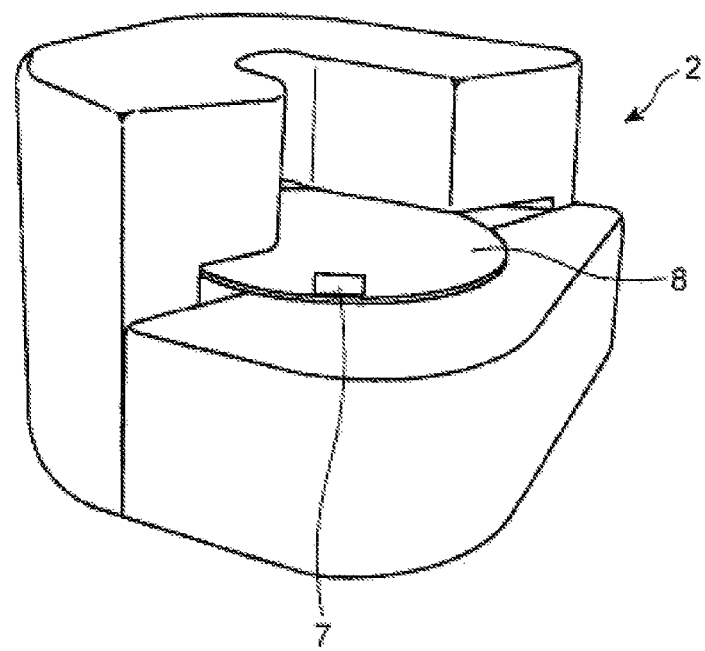
FIG. 2 is a perspective view of the measurement device in FIG. 1.

In FIG. 1, the measurement device of the embodiment of the present invention measures an organism as the measurement subject, and is configured from a main unit part 2, on which the organism that is the subject of measurement (in the example illustrated, a mouse M) is loaded, a control part 3 that performs operational control of all parts of main unit part 2, and a display part 4 that displays processing results, etc. from control part 3.

Main unit part 2 includes a first external magnetic field generation device 5 with a low magnetic field as a first magnetic field generation device, a second external magnetic field generation device 6 with a high magnetic field as a second magnetic field generation device, a cylindrical RF coil (resonator) 7, and a rotating table 8 as a rotating movement device for rotating around a vertical axis. The rotating table 8 is driven rotationally by a rotational drive mechanism 9 configured from a motor, pulley, belt, etc.

Figure 3:
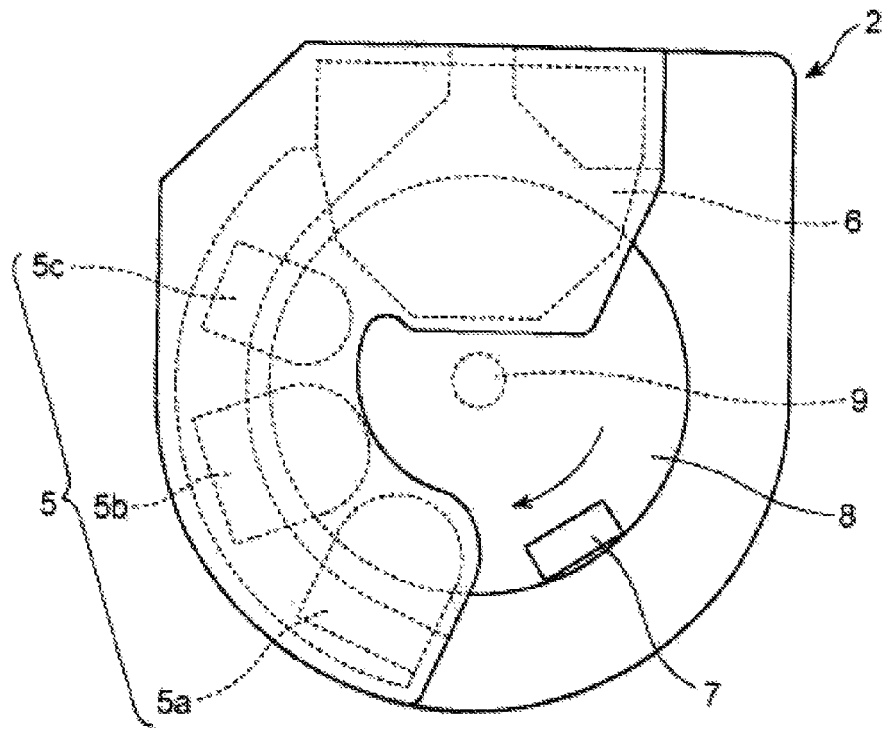
FIG. 3 is a plan view of the measurement device in FIG. 2.

RF coil 7 is fixed on the peripheral part of rotating table 8. The organism that is the subject of measurement is held within RF coil 7, and, by being moved rotationally along with rotating table 8, passes sequentially through the magnetic fields of first external magnetic field generation device 5 and second external magnetic field generation device 6. In the example of FIG. 3, rotating table 8 rotates clockwise. RF coil 7 forms an electromagnetic wave magnetic field oriented perpendicular to the static magnetic fields of first external magnetic field generation device 5 and second external magnetic field generation device 6.

First external magnetic field generation device 5, in the present embodiment, is made up of three external magnetic field generation devices 5a, 5b, and 5c, and each of these includes a permanent magnet 50, a magnetic field gradient coil 51, and a magnetic sweep coil 52. This first external magnetic field generation device 5 provides the excited field for OMRI in the space through which RF coil 7 passes on rotating table 8. Free radical electron spin is excited by this first external magnetic field generation device 5 in order to perform OMRI measurement with second external magnetic field generation device 6.

Second external magnetic field generation device 6 includes a permanent magnet 60 for generation a static magnetic field in the space through which RF coil 7 passes on rotating table 8. Moreover, a magnetic field gradient coil 61 is provided, so that a magnetic field gradient of a set scale can be generated at a set frequency of occurrence according to the set MR pulse sequence in the static magnetic field generated by permanent magnet 60. This second external magnetic field generation device 6 provides an external static magnetic field for MRI/OMRI. MRI measurement and OMRI measurement are performed by this second external magnetic field generation device 6.

First external magnetic field generation device 5 is connected to control part 3 by way of a first static magnetic field generation driver 10. A power supply not shown in the drawings is connected to this first static magnetic field driver 10 in order to supply power to magnetic field gradient coil 51 and magnetic field sweep coil 52. First static magnetic field generation driver 10 controls magnetic field gradient coil 51 and magnetic field sweep coil 52 in accordance with instructions from control part 3. The strength of the magnetic field of first external magnetic field generation device 5 in the present embodiment is 20 mT, but the strength of this magnetic field can be set as desired within the ranges of greater than 0 and no more than 50 mT for OMRI, and greater than 0 and no more than 11 T for MRI. Moreover, it is also possible to use an electromagnet in place of permanent magnet 60.

Second external magnetic field generation device 6 is connected to control part 3 by way of a second static magnetic field generation driver 11. This second static magnetic field generation driver 11 is connected to a power supply not shown in the drawings in order to supply power to magnetic field gradient coil 61. Second static magnetic field generation driver 11 drives magnetic field gradient coil 61 in accordance with instructions from control part 3. The strength of the magnetic field of second external magnetic field generation device 6 in the present embodiment is 1.5 T, but the strength of this magnetic field can be set as desired within this range of greater than 0 and no more than 11 T, with larger values being preferable. A permanent magnet 60 is used in the present embodiment, but if a permanent magnet 60 is used, the strength of its magnetic field may be made as great as 2 T. Moreover, it is also possible to use a superconductor magnet in place of permanent magnet 60. If a superconductor magnet is used in place of permanent magnet 60, the strength of its magnetic field may be made as great as 11 T.

RF coil 7 is connected to control part 3 by way of an RF coil driver 12 and a detection signal receiver part 13. Moreover, rotational drive mechanism 9 is connected to control part 3 by way of a rotational drive mechanism driver 14. A power supply not shown in the drawings is connected to RF coil driver 12 and rotational drive mechanism driver 14 in order to supply power to RF coil 7 and rotational drive mechanism 9, respectively.

RF coil driver 12 and rotational drive mechanism driver 14 drive RF coil 7 and rotational drive mechanism 9, respectively, in accordance with sequences directed by control part 3. At this time, RF coil driver 12, in synchronization with rotational drive driver 10, drives RF coil 7 in the same timing at which RF coil 7, along with rotating table 8, passes through the magnetic fields of first magnetic field generation device 5 and second magnetic field generation device 6. When high-frequency pulses are impressed on RF coil 7, a high-frequency magnetic field is generated in RF coil 7, and the organism that is the subject of measurement inside is exposed to the high-frequency magnetic field.

The electron spin resonance signal received by RF coil 7 in first external magnetic field generation device 5, and the magnetic resonance signal received by RF coil 7 in the second external magnetic field generation device 6, are each received by detection signal receiver part 13 and passed on to control part 3. It is preferable for the drive time from first external magnetic field generation device 5 to second external magnetic field generation device 6 to be within 1 second, and more preferable for it to be within 0.7 seconds; in the present embodiment it is set to be 0.5 seconds.

Moreover, a measurement sequence processing part 30, an OMRI measurement processing part 31, and an MRI measurement processing part 32 are provided in control part 3. The measurement sequence control part 30 includes power supply control sequences for the first external magnetic field generation device 5, the second external magnetic field generation device 6, the RF coil 7, and the rotational drive mechanism 9, as well as a measurement sequence for the RF coil 7, and it controls the first external magnetic field generation device 5, the second external magnetic field generation device 6, the RF coil 7, and the rotational drive mechanism 9. OMRI measurement processing part 31 and MRI measurement processing part 32 perform image processing based on electron spin resonance signals and magnetic resonance signals obtained in accordance with the measurement sequence, and the results thereof are displayed on display device 4.

Moreover, in the present embodiment, this image processing is such that it is possible to synthesize multiple nitroxyl probes with differing localizations within the organism (for instance, with differing membrane permeability), and label these with $^{14}N$ and $^{15}N$, respectively, to perform separate simultaneous image analysis of minute spaces by way of bonding with cell membranes (of nanometer thickness) or receptors, etc. Control part 3 actually consists of a computer system, and functions as described above by executing computer programs stored on a recording medium such as a hard disk, etc.

Next, the operation of the measurement device 1 with the configuration mentioned above will be described. First, a small animal, for instance a mouse M, is placed as the organism that is the subject of measurement in RF coil 7 on rotating table 8. In this example, redox metabolism abnormalities of oxidative stress disorders, or brain function in schizophrenia, etc. in the organism that is the subject of measurement are subjected to spatial image analysis.

Next, rotating table 8 is rotated by driving rotating drive mechanism 9, and the organism to be measured is made to rotate sequentially through the magnetic fields of the first magnetic field generation device 5 and the second magnetic field generation device 6. At this time, by radiating high-frequency waves from the RF coil 7 and driving magnetic field sweep coil 52 in first magnetic field generation device 5, the static magnetic field is swept at high speed. By doing this, unpaired electrons in the organism to be measured absorb the high-frequency waves, and electron spin is resonantly excited.

The organism that is the subject of measurement, which has passed through first external magnetic field generation device 5, next enters the second external magnetic field generation device 6, and is placed in an extremely strong static magnetic field of 1 T or greater, which is 1.5 T in the present embodiment. By doing this, the electron spin resonantly excited in the first external magnetic field generation device 5 undergoes a transition into nuclear spin energy. Next, using RF coil 7, the signal obtained from the organism that is the subject of measurement using high-frequency radiation is received by detection signal receiver part 13.

The signal received in this way by detection signal receiver part 13 is accepted by control part 3, and processed by OMRI measurement processing part 31 and MRI measurement processing part 32. MRI measurement processing part 32 synthesizes an MRI image by processing the signals obtained from RF coil 7 in second external magnetic field generation device 5. Moreover, OMRI measurement processing part 31 synthesizes images showing nuclear spin distribution by processing signals obtained from second external magnetic field generation device 5.

As described above, with the measurement device 1 of the present embodiment, it is possible to cause the first external magnetic field generation device 5 and the second external magnetic field generation device 6 to generate magnetic fields of differing size, to cause the organism that is the subject of measurement to move rotationally using rotating table 8, and to obtain MRI images and OMRI images while causing the organism that is the subject of measurement to pass through the magnetic fields of the first and second external magnetic field generation devices 5 and 6 sequentially. Thus, the organism that is the subject of measurement is not made to move repetitively, and there is no load imposed on it by moving and stopping.

Moreover, with this measurement device 1, the first external magnetic field generation device 5, with a low magnetic field, is used as an OMRI electron spin excitation device, and the second external magnetic field generation device 5, with a high magnetic field, is used as an MRI and OMRI external magnetic field generation device. Thus, with this measurement device 1, since OMRI measurement is performed by the second external magnetic field generation device 6, with a high magnetic field, after electron spin is excited by the first external magnetic field generation device 5, with a low magnetic field, the OMRI external magnetic field becomes extremely large, and it is possible to obtain high-sensitivity, high-resolution OMRI images.

In this measurement device 1, it is also possible to cause rotating table 8 to rotate in reverse, and perform measurement while causing the organism that is the subject of measurement to pass through the second external magnetic field generation device 6 and first external magnetic field generation device 5 sequentially. In this case, the second external magnetic field generation device 6, with a high magnetic field, can be used as an MRI external magnetic field generation device, and the first external magnetic field generation device 5, with a low magnetic field, can be used as an OMRI external magnetic field generation device.

By doing this, MRI images can be obtained by the second external magnetic field generation device 6, and OMRI images can be obtained by the first external magnetic field generation device 5.

Moreover, the configuration of the measuring device 1 of the present embodiment is such that the organism that is the subject of measurement is caused to move rotationally by rotating table 8, but it is also possible to use a configuration wherein, conversely, the organism that is the subject of measurement is not made to move rotationally, but rather the first and second external magnetic field generation devices 5 and 6 are made to move rotationally. In this case, since the organism that is the subject of measurement remains still, it feels no discomfort during measurement, allowing a measurement device to be realized that is gentle to the organism. Moreover, since, in this case, the first and second external magnetic field generation devices 5 and 6 need not be moved repetitively, there is no load imposed when moving or stopping the external magnetic field generation devices.

Moreover, the measurement device 1 in the present embodiment is MRI/OMRI, but it can be applied to any device that causes an organism that is the subject of measurement to move between two or more external magnetic field generation devices that generate magnetic fields of different sizes. Moreover, with the measurement device 1 of the present embodiment, it is also possible to perform continuous measurement of multiple measurement items by providing other measurement devices, such as X-ray and CT (Computed Tomography) devices, ultrasound imaging devices, positron tomography (PET: Positron Emission Tomography) devices, etc on the rotational movement path of the organism that is the subject of measurement on rotating table 8 as discussed in greater detail below.

Moreover, with this measurement device 1, it is possible to obtain not only redox dynamics images as functional images of an organism, but also histological images as structural images. Furthermore, it is also possible to obtain structural images of the structure, defects, etc. of objects other than organisms, for instance, semiconductors, etc., and it is possible to obtain images such as functional images, structural images, etc. of measurement subjects using a variety of types of magnetic resonances, such as electron spin resonance, nuclear magnetic resonance, etc.

Figure 4A:
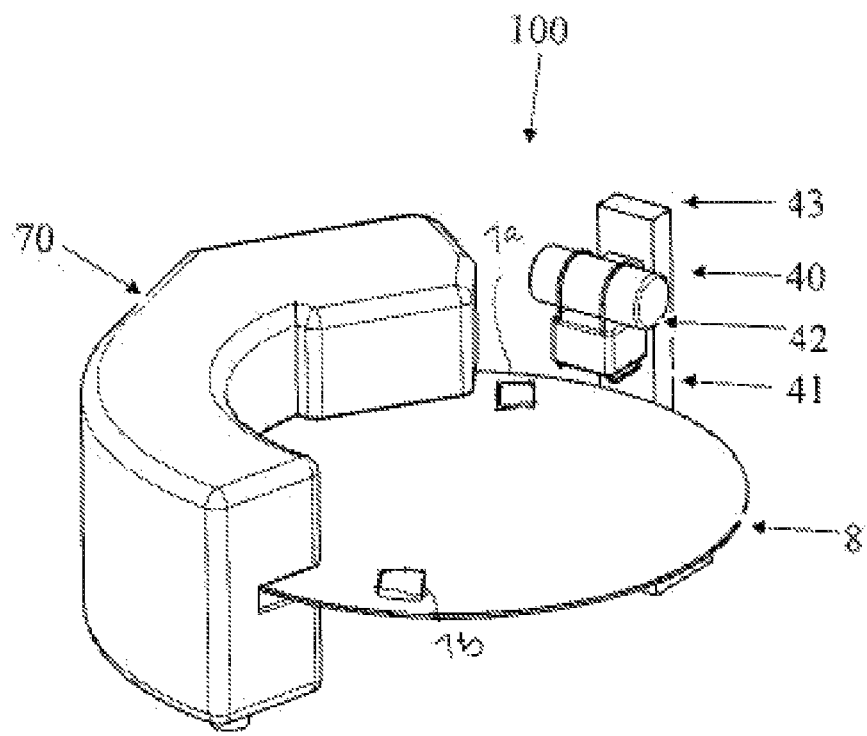
FIG. 4A is a perspective view of a measurement system according to a second embodiment of the present invention.
Figure 4B:
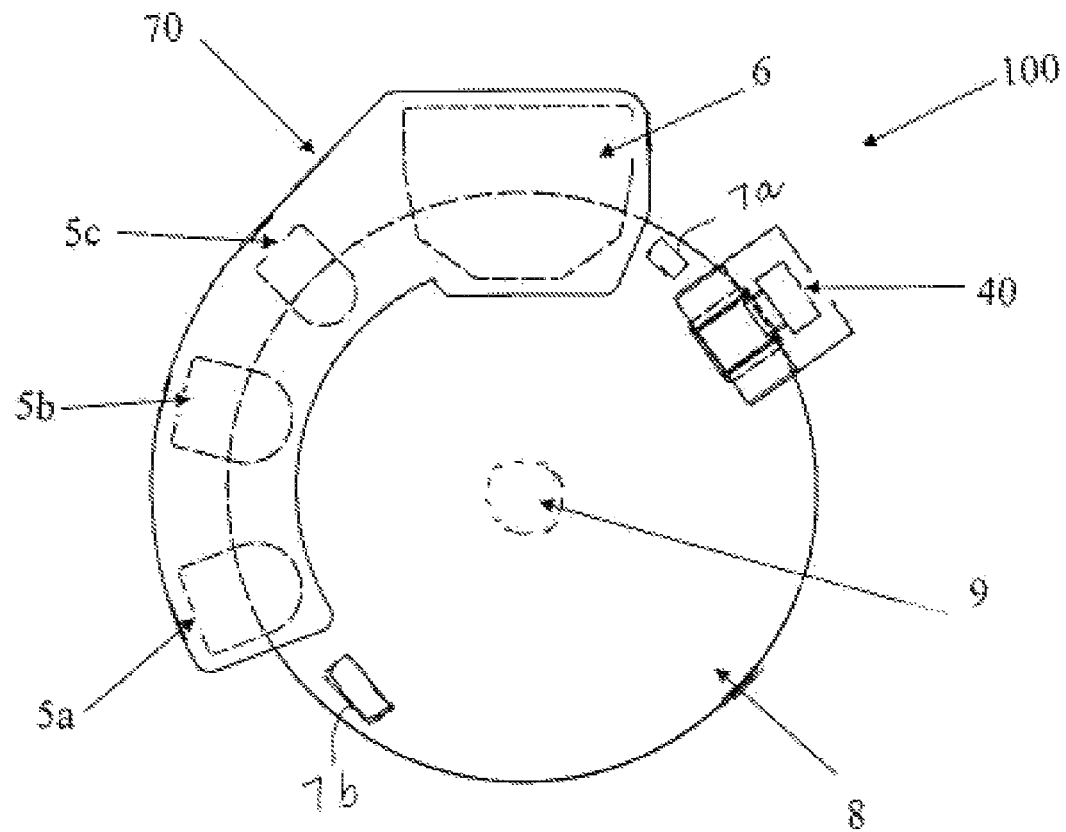
FIG. 4B is a plan view of the measurement system illustrated in FIG. 4A.

FIG. 4A is a perspective view of an exemplary embodiment of a measurement system 100 according to a second embodiment of the present invention. FIG. 4B is a plan view of the measurement system 100 illustrated in FIG. 4A. Measurement system 100 includes a first imaging assembly (external magnetic field generation devices 5 and 6) 70, a second imaging assembly (x-ray machine 40), cylinder RF coils 7a and 7b and rotating table 8 rotated by rotational drive mechanism 9. As illustrated, RF coil 7a is fixed on the periphery of rotating table 8 to the left of x-ray machine 40 and RF coil 7b is fixed on the periphery of rotating table 8 to the right of external magnetic field generation device 5a. The RF coils 7a and 7b are configured to accommodate measurement objects M1 and M2, respectively, having a diameter preferably of 1 cm to 7 cm for small animals and objects having a diameter of 20 cm to 40 cm for human body parts, for example.

As illustrated in FIG. 9 which is discussed in greater detail below, RF coil 7a is connected to control part 3a through RF coil driver 12a and detection signal receiver part 13a and RF coil 7b is connected to control part 3a through RF coil driver 12b and detection signal receiver part 13b. Also, rotational drive mechanism 9 is connected to the control part 3a through the rotational drive mechanism driver 14. RF coil drivers 12a and 12b and rotation drive mechanism driver 14 are connected to a power source (not shown) which supplies power to the RF coils 7a and 7b and the rotational drive mechanism 9.

RF coil drivers 12a and 12b along with the rotational drive mechanism driver 14, follow sequences in the form of steps of a computer program, for example, provided by control part 3a and activate the RF coils 7a and 7b and the rotational drive mechanism 9, respectively. At this point, the RF coil drivers 12a and 12b are synchronized with the rotational drive mechanism driver 14, such that the RF coil 7a is properly aligned under the x-ray machine 40 at the time the RF coil 7b is properly aligned under the external magnetic field generation device 5a. At this point, the control part 3a using software of the measurement sequence processing part 30, recognizes that the coil 7b should be driven by RF coil driver 12b and thus power is supplied to coil 7b making coil 7b an RF coil, such that when high-frequency pulses are impressed on RF coil 7b, a high-frequency magnetic field is generated in RF coil 7b, and the organism that is the subject of measurement inside is exposed to the high-frequency magnetic field.

Conversely, when RF coil 7a is properly aligned under the x-ray machine 40, no power is provided to RF coil 7a by control part 3a and thus, RF coil 7a acts only as a holder for the organism that is the subject of measurement for the x-ray machine 40.

The alignment of these coils can include various sensors and guides provided with the first and second imaging assemblies. After the measurement objects M1 and M2 have been imaged by the x-ray machine 40 and the first imaging assembly 70, respectively, the measurement objects advance to their next location as determined by control part 3a. Imaging of the measurement objects can occur simultaneously or at separate times. For example, measurement object M1 advances to a first waiting position (e.g., a non-imaging position) while measurement object M2 advances to external magnetic field generation device 5b. Measurement object M1 advances through several non-imaging positions until measurement object M2 has exited the first imaging assembly 70. Afterwards, measurement object M2 is imaged by x-ray machine 40 while measurement object M2 is measured by the first imaging assembly 70. Again, the control part 3a will recognize that RF coil 7b, which is now properly aligned under the x-ray machine 40 will not receive power and acts as a holder for the measurement object M2, while RF coil 7a which is now properly aligned under the first imaging assembly 70, will be driven by RF coil driver 12a making coil 7a an RF coil.

In general, the x-ray machine 40 takes several seconds for imaging while the external magnetic field generation device 5 take several milliseconds and the external magnetic field generation device 6 takes between several seconds to several minutes for imaging.

First imaging assembly (external magnetic field generation devices 5 and 6) 70 operates in substantially a similar manner discussed above with the first embodiment of the present invention except for the measurement object is stopped while being measured as it moves through the external magnetic field generation devices 5 and 6. This is because the first imaging assembly is provided in combination with an imaging assembly (x-ray machine 40) that requires the measurement object to remain still while being imaged. The x-ray machine 40 operates by observing the absorption of radiation on the measurement object M. According, the x-ray machine 40 includes a control device 42, a radiation device 41 and a housing 43 to support the control device 42 and the radiation device 41. Control device 42 communicates with control part 3a to operate the x-ray machine 40 and to process the image to be shown on display part 4. According to an alternative embodiment of the present invention, x-ray machine 40 may only include the radiation device 41 and an imaging assembly driver (not shown) may be provided such that the x-ray machine 40 communicates directly with the control part 3a.

With the arrangement of the first and second imaging assemblies illustrated in FIGS. 4A and 4B, the distance between the external magnetic field generation device 6 of the first imaging assembly 70 and the x-ray machine 40 is approximately 50 cm or more. Alternatively if the x-ray machine 40 was provided to the right of the first imaging assembly 70 (i.e., close to the external magnetic field generation device 5a) then the distance between the external magnetic field generation device 5c and the x-ray machine 40 is approximately 10 cm or more. If the first imaging assembly 70 and the x-ray machine 40 are provided closer to each other than the distance specified above, the magnetic field generated by the first imaging assembly 70 will cause the x-ray machine 40 to not work properly causing distortion in the images produced by the x-ray machine 40 and the metal materials provided in the x-ray machine will distort the magnetic field of the first imaging assembly 70 causing image distortion of the images produced by the first imaging assembly 70.

As illustrated in the second embodiment of the present invention, two measurement objects M1 and M2 are provided. According to a modification of the second embodiment of the present invention, more than two measurement objects are provided with the measurement system 100. Control part 3a would be modified to accommodate the more than two measurement objects such that these measurement objects are synchronized with the first and second imaging assemblies. According to another modification of the present invention, it is possible to cause rotating table 8 to rotate in reverse and perform imaging in reverse order.

Figure 5A:
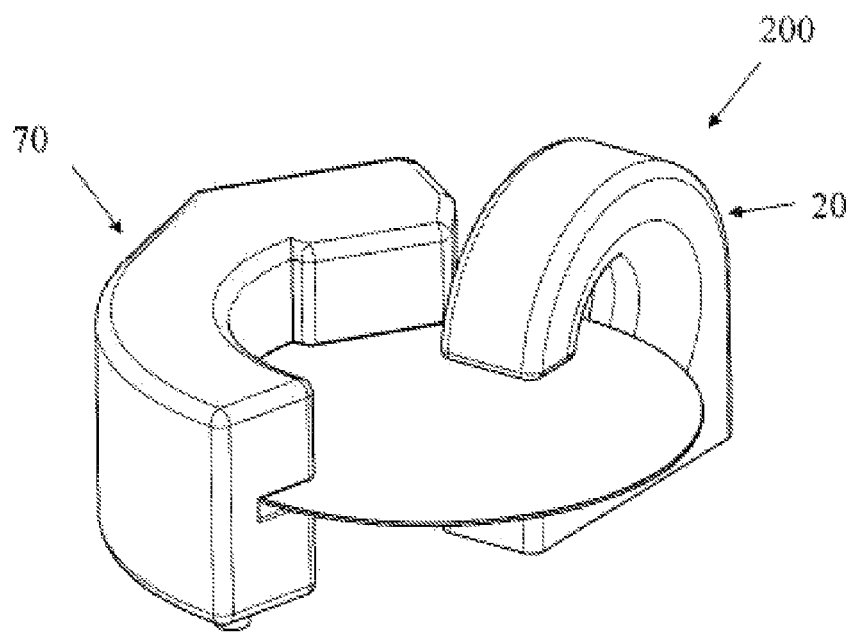
FIG. 5A is a perspective view of a measurement system according to a third embodiment of the present invention.
Figure 5B:
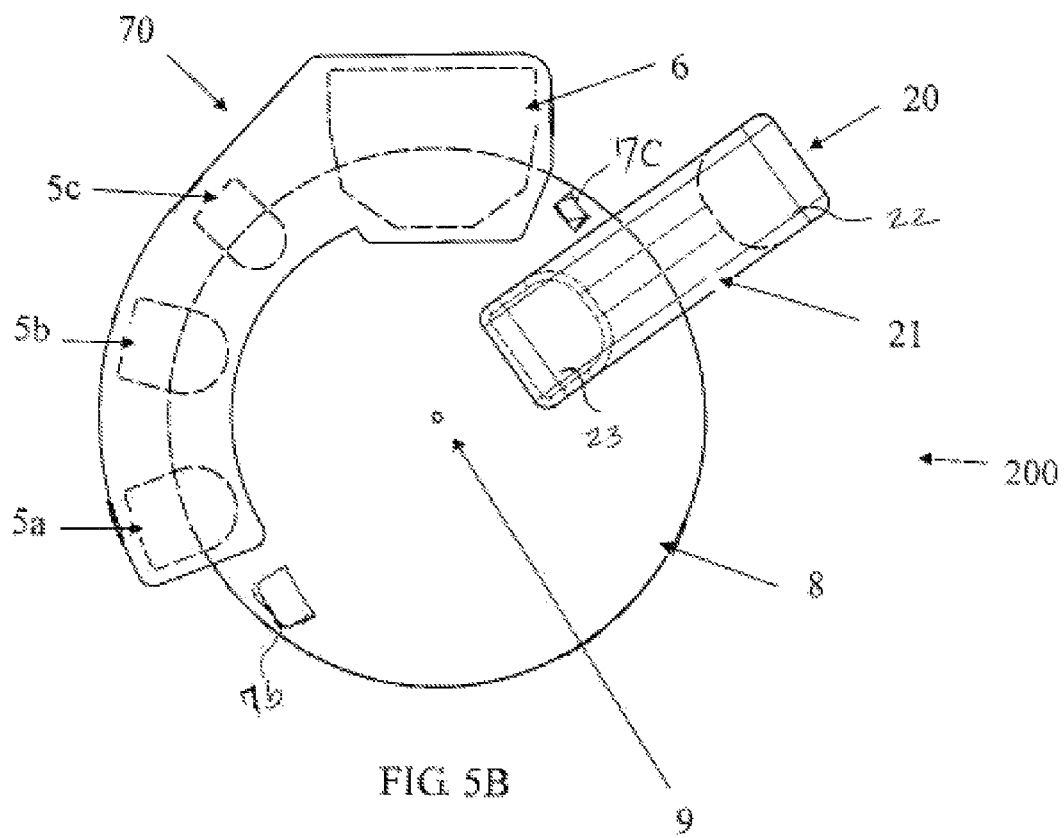
FIG. 5B is a plan view of the measurement system illustrated in FIG. 5A.

FIG. 5A is a perspective view of an exemplary embodiment of a measurement system 200 according to a third embodiment of the present invention. FIG. 5B is a plan view of the measurement system 200 illustrated in FIG. 5A. Measurement system 200 includes a first imaging assembly (external magnetic field generation devices 5 and 6) 70, a second imaging assembly (CT system 20), cylinder RF coils 7b and 7c and rotating table 8 rotated by rotational drive mechanism 9. First imaging assembly (external magnetic field generation devices 5 and 6) 70 operates in substantially a similar manner discussed above with the first embodiment of the present invention except for the measurement object is stopped while being measured as it moves through the external magnetic field generation devices 5 and 6. This is because the first imaging assembly is provided in combination with an imaging assembly (CT system 20) that requires the measurement object to remain still while being imaged. CT system 20 generally includes a housing 21, a plurality of a radiation devices such as radiation device 22, a plurality of detectors such as detector 23 and a control unit (not shown) which communicates with control part 3a to process images to be shown on display part 4. As illustrated, RF coil 7c is fixed on the periphery of rotating table 8 to the left of CT system 20 and RF coil 7b is fixed on the periphery of rotating table 8 to the right of external magnetic field generation device 5a. The RF coils 7b and 7c are configured to accommodate measurement objects M1 and M2 having a diameter preferably of 1 cm to 7 cm for small animals and objects having a diameter of 20 cm to 40 cm for human body parts, for example.

As illustrated in FIG. 9, RF coil 7c is connected to control part 3a through RF coil driver 12c and detection signal receiver part 13c and RF coil 7b is connected to control part 3a through RF coil driver 12b and detection signal receiver part 13b. Also, rotational drive mechanism 9 is connected to the control part 3a through the rotational drive mechanism driver 14. RF coil drivers 12b and 12c and rotation drive mechanism driver 14 are connected to a power source which supplies power to the RF coils 7b and 7c and the rotational drive mechanism 9.

RF coil drivers 12b and 12c along with the rotational drive mechanism driver 14, follow sequences in the form of steps of a computer program, for example, provided by control part 3a and activate the RF coils 7b and 7c and the rotational drive mechanism 9. At this point, the RF coil drivers 12b and 12c are synchronized with the rotational drive mechanism driver 14, such that the RF coil 7c is properly aligned under the CT system 20 at the time the RF coil 7b is properly aligned under the external magnetic field generation device 5a. At this point, the control part 3a recognizes that the coil 7b should be driven by RF coil driver 12b and thus power is supplied to coil 7b making coil 7b an RF coil, such that when high-frequency pulses are impressed on RF coil 7b, a high-frequency magnetic field is generated in RF coil 7b, and the organism that is the subject of measurement inside is exposed to the high-frequency magnetic field.

Conversely, when RF coil 7c is properly aligned under CT system 20, no power is provided to RF coil 7c by control part 3a and thus, RF coil 7c acts only as a holder for the organism that is the subject of measurement for the CT system 20. The alignment of these coils can include various sensors and guides provided with the first and second imaging assemblies. After the measurement objects M1 and M2 have been imaged by the CT system 20 and the first imaging assembly 70, respectively, the measurement objects advance to their next location as determined by the control part 3a as discussed in detail above. Imaging of the measurement objects can occur simultaneously or at separate times.

In general, the CT system 20 takes dozens of seconds, for example, 5 seconds to 40 seconds for imaging while the external magnetic field generation device 5 take several milliseconds and the external magnetic field generation device 6 takes between several seconds to several minutes for imaging. With the arrangement of the first and second imaging assemblies illustrated in FIGS. 5A and 5B, the distance between the external magnetic field generation device 6 of the first imaging assembly 70 and the CT system 20 is approximately 50 cm or more. Alternatively, if the CT system 20 was provided to the right of the first imaging assembly 70 (i.e., close to the external magnetic field generation device 5a) then the distance between the external field generation device 5c and the CT system 20 is approximately 10 cm or more. If the first imaging assembly 70 and the CT system 20 are provided closer to each other than the distance specified above, the magnetic field generated by the first imaging assembly 70 will cause the CT system 20 not to work properly causing distortion in the images produced by the CT system 20 and the metal materials provided in the CT system 20 will distort the magnetic field of the first imaging assembly 70 causing image distortion of the images produced by the first imaging assembly 70.

As illustrated in the third embodiment of the present invention, two measurement objects M1 and M2 are provided. According to a modification of the third embodiment of the present invention, more than two measurement objects are provided with the measurement system 200. Control part 3a would be modified to accommodate the more than two measurement objects such that these measurement objects are synchronized with the first and second imaging assemblies. According to another modification of the present invention, it is possible to cause rotating table 8 to rotate in reverse and perform imaging in reverse order.

Figure 6A:
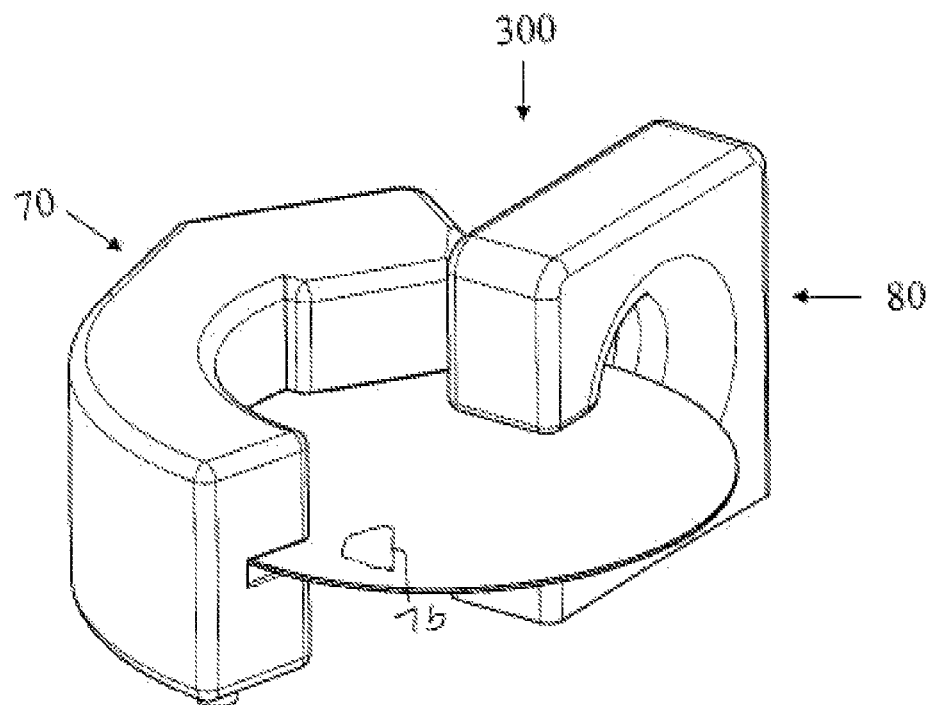
FIG. 6A is a perspective view of a measurement system according to a fourth embodiment of the present invention.
Figure 6B:
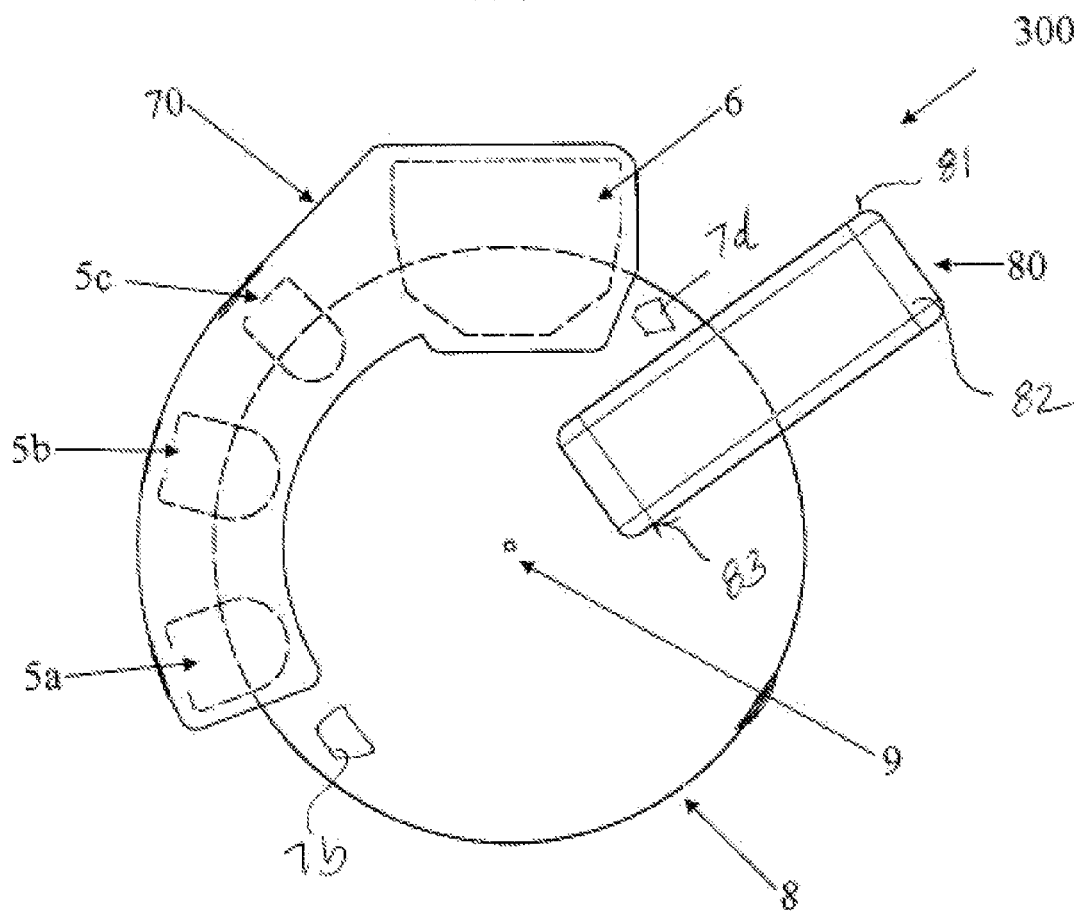
FIG. 6B is a plan view of the measurement system illustrated in FIG. 6A.

FIG. 6A is a perspective view of an exemplary embodiment of a measurement system 300 according to a fourth embodiment of the present invention. FIG. 6B is a plan view of the measurement system 300 illustrated in FIG. 6A. Measurement system 300 includes a first imaging assembly (external magnetic field generation devices 5 and 6) 70, a second imaging assembly (PET system 80), cylinder RF coils 7b and 7d and rotating table 8 rotated by rotational drive mechanism 9. First imaging assembly (external magnetic field generation devices 5 and 6) 70 operates in substantially a similar manner discussed above with the first embodiment of the present invention except for the measurement object is stopped while being measured as it moves through the external magnetic field generation devices 5 and 6. This is because the first imaging assembly is provided in combination with an imaging assembly (PET system 80) that requires the measurement object to remain still while being imaged. PET system 80 generally includes a housing 81, a plurality of a radiation devices such as radiation device 82, a plurality of detectors such as detector 83 and a control unit (not shown) which communicates with control part 3a to process images to be shown on display part 4. As illustrated, RF coil 7d is fixed on the periphery of rotating table 8 to the left of PET system 80 and RF coil 7b is fixed on the periphery of rotating table 8 to the right of external magnetic field generation device 5a. The RF coils 7b and 7d are configured to accommodate measurement objects M1 and M2 having a diameter preferably of 1 cm to 7 cm for small animals and objects having a diameter of 20 cm to 40 cm for human body parts, for example.

As illustrated in FIG. 9, RF coil 7d is connected to control part 3a through RF coil driver 12d and detection signal receiver part 13d and RF coil 7b is connected to control part 3a through RF coil driver 12b and detection signal receiver part 13b. Also, rotational drive mechanism 9 is connected to the control part 3a through the rotational drive mechanism driver 14. RF coil drivers 12b and 12d and rotation drive mechanism driver 14 are connected to a power source which supplies power to the RF coils 7b and 7d and the rotational drive mechanism 9.

RF coil drivers 12b and 12d along with the rotational drive mechanism driver 14, follow sequences in the form of steps of a computer program, for example, provided by control part 3a and activate the RF coils 7b and 7d and the rotational drive mechanism 9. At this point, the RF coil drivers 12b and 12d are synchronized with the rotational drive mechanism driver 14, such that the RF coil 7d is properly aligned under the PET system 80 at the time the RF coil 7b is properly aligned under the external magnetic field generation device 5a. At this point, the control part 3a recognizes that the coil 7b should be driven by RF coil driver 12b and thus power is supplied to coil 7b making coil 7b an RF coil, such that when high-frequency pulses are impressed on RF coil 7b, a high-frequency magnetic field is generated in RF coil 7b, and the organism that is the subject of measurement inside is exposed to the high-frequency magnetic field.

Conversely, when RF coil 7d is properly aligned under PET system 80, no power is provided to RF coil 7d by control part 3a and thus, RF coil 7d acts only as a holder for the organism that is the subject of measurement for the PET system 80. The alignment of these coils can include various sensors and guides provided with the first and second imaging assemblies. After the measurement objects M1 and M2 have been imaged by the PET system 80 and the first imaging assembly 70, respectively, the measurement objects advance to their next location as determined by the control part 3*a* as discussed in detail above. Imaging of the measurement objects can occur simultaneously or at separate times.

In general, the PET system 80 takes dozens of seconds, for example, 5 seconds to 40 seconds for imaging while the external magnetic field generation device 5 take several milliseconds and the external magnetic field generation device 6 takes between several seconds to several minutes for imaging. With the arrangement of the first and second imaging assemblies illustrated in FIGS. 6A and 6B, the distance between the external magnetic field generation device 6 of the first imaging assembly 70 and the PET system 80 is approximately 50 cm or more. Alternatively if the PET system 80 was provided to the right of the first imaging assembly 70 (i.e., close to the external magnetic field generation device 5*a*) then the distance between the external field generation device 5*c* and the PET system 80 is approximately 10 cm or more. If the first imaging assembly 70 and the PET system 80 are provided closer to each other than the distance specified above, the magnetic field generated by the first imaging assembly 70 will cause the PET system 80 not to work properly causing distortion in the images produced by the PET system 80 and the metal materials provided in the PET system 80 will distort the magnetic field of the first imaging assembly 70 causing image distortion of the images produced by the first imaging assembly 70.

As illustrated in the fourth embodiment of the present invention, two measurement objects M1 and M2 are provided. According to a modification of the fourth embodiment of the present invention more than two measurement objects can be provided with the measurement system 300. Control part 3*a* would be modified to accommodate the more than two measurement objects such that these measurement objects are synchronized with the first and second imaging assemblies. According to another modification of the present invention, it is possible to cause rotating table 8 to rotate in reverse and perform imaging in reverse order.

Figure 7A:
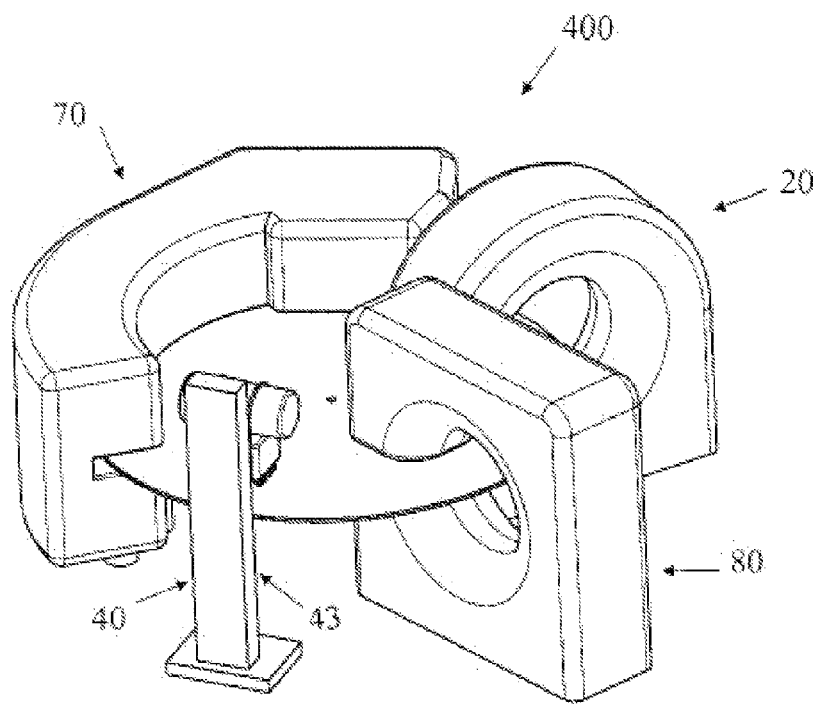
FIG. 7A is a perspective view of a measurement system according to a fifth embodiment of the present invention.
Figure 7B:
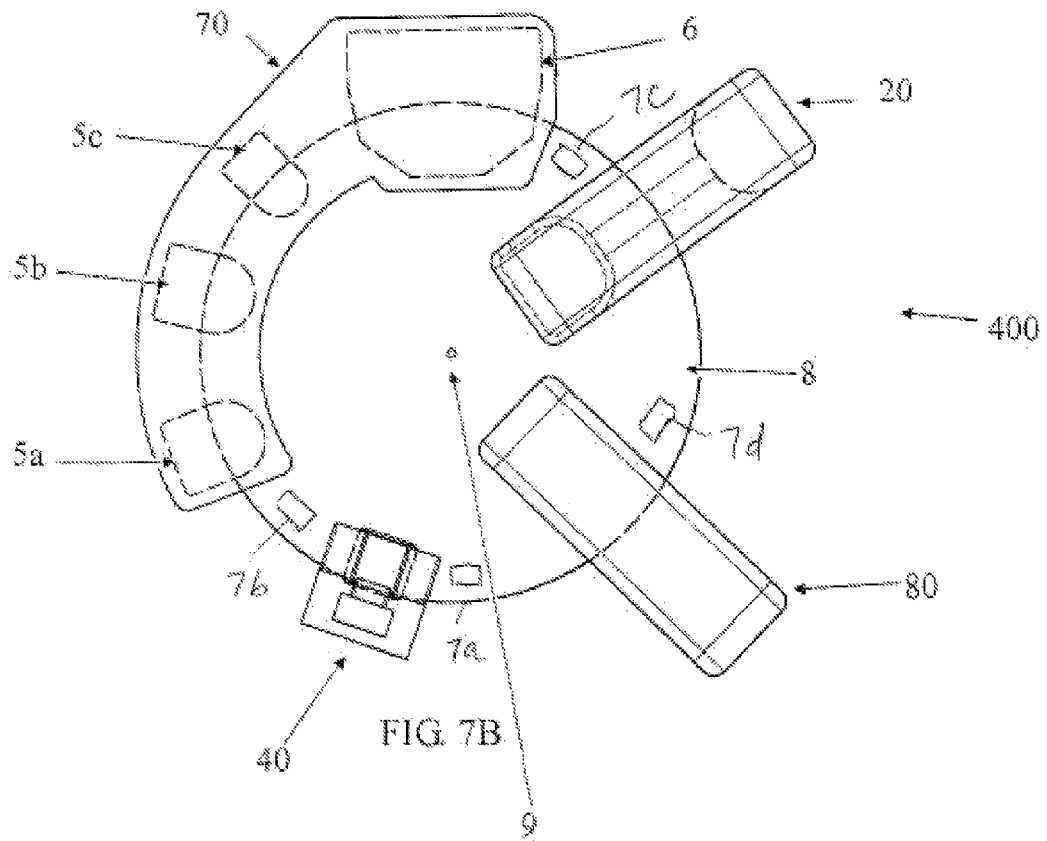
FIG. 7B is a plan view of the measurement system illustrated in FIG. 7A.

FIG. 7A is a perspective view of an exemplary embodiment of a measurement system 400 according to a fifth embodiment of the present invention. FIG. 7B is a plan view of the measurement system 400 illustrated in FIG. 7A. Measurement system 400 includes a first imaging assembly (external magnetic field generation devices 5 and 6) 70, a second imaging assembly (x-ray machine 40), a third imaging assembly (PET system 80), a fourth imaging assembly (CT system 20), cylinder RF coils 7*a*, 7*b*, 7*c* and 7*d* and rotating table 8 rotated by rotational drive mechanism 9. First imaging assembly (external magnetic field generation devices 5 and 6) 70 operates in substantially a similar manner discussed above with the first embodiment of the present invention except for the measurement object is stopped while being measured as it moves through the external magnetic field generation devices 5 and 6. This is because the first imaging assembly is provided in combination with imaging assemblies (x-ray machine 40, PET system 80 and CT system 20) that require the measurement object to remain still while being imaged. As illustrated in FIG. 9, the RF coil drivers 12*a*, 12*b*, 12*c* and 12*d* are synchronized with the rotational drive mechanism driver 14, such that each of the RF coils is properly aligned under the corresponding imaging assembly. The alignment of these RF coils can include various sensors and guides provided with the imaging assemblies. After the measurement objects M1, M2, M3 and M4 have been imaged by their respective imaging assemblies, the measurement objects advance to their next location as determined by the control part 3*a*. Imaging of the measurement objects can occur simultaneously or at separate times.

For example, assume measurement objects M1, M2, M3 and M4 are originally positioned at CT system 20, PET system 80, x-ray machine 40 and external magnetic field generation device 5*a*, respectively, and each has been imaged by their respective imaging assemblies, after the imaging assembly that takes the longest time to finish imaging its measurement object, the rotating table 8 rotates such that the measurement objects advance to their next position. The measurement object's next position could be the next imaging assembly or a non-imaging position (e.g., the measurement object is not positioned under an imaging assembly) as determined by the control part 3*a*. Alternatively, the measurement object could rotate to the next imaging assembly but the imaging assembly may not image the measurement object as instructed by the control part 3*a*. Thus, this action could also function as a non-imaging position for the measurement object. According to an embodiment of the present invention, one or many measurement objects could be used with the measurement system. Therefore, in the case of one measurement object being measured by the different imaging assemblies, only one RF coil would be needed to hold to measurement object which rotates around the different imaging assemblies.

In general, the x-ray machine 40 takes several seconds for imaging while the CT system 20 and the PET system 80 each takes dozens of seconds, for example, 5 seconds to 40 seconds for imaging. The external magnetic field generation device 5 take several milliseconds and the external magnetic field generation device 6 takes between several seconds to several minutes for imaging. With the arrangement of the first through fourth imaging assemblies illustrated in FIGS. 7A and 7B, the distances between each of the x-ray machine 40, CT system 20 and PET system 80 is approximately 10 cm or more and the distance between the external magnetic field generation device 6 of the first imaging assembly 70 and the CT system 20 is approximately 50 cm or more and the distance between the external field generation device 5*c* and x-ray machine 40 is approximately 10 cm or more. Providing the imaging assemblies closer to each other than the distances specified above, creates distorted images.

Although the imaging assemblies are arranged in a specific order as illustrated in FIGS. 7A and 7B, the imaging assemblies can be arranged in any order around rotating table 8 as along as the distances between the imaging assemblies as discussed above is maintained. With that said, the second, third or fourth imaging assembly can be arranged next to the external magnetic field generation device 6 or the external magnetic field generation device 5*c*. The imaging assembly located next to one of these external magnetic generation devices would have to be located within the specified distance discussed above.

Figure 8:
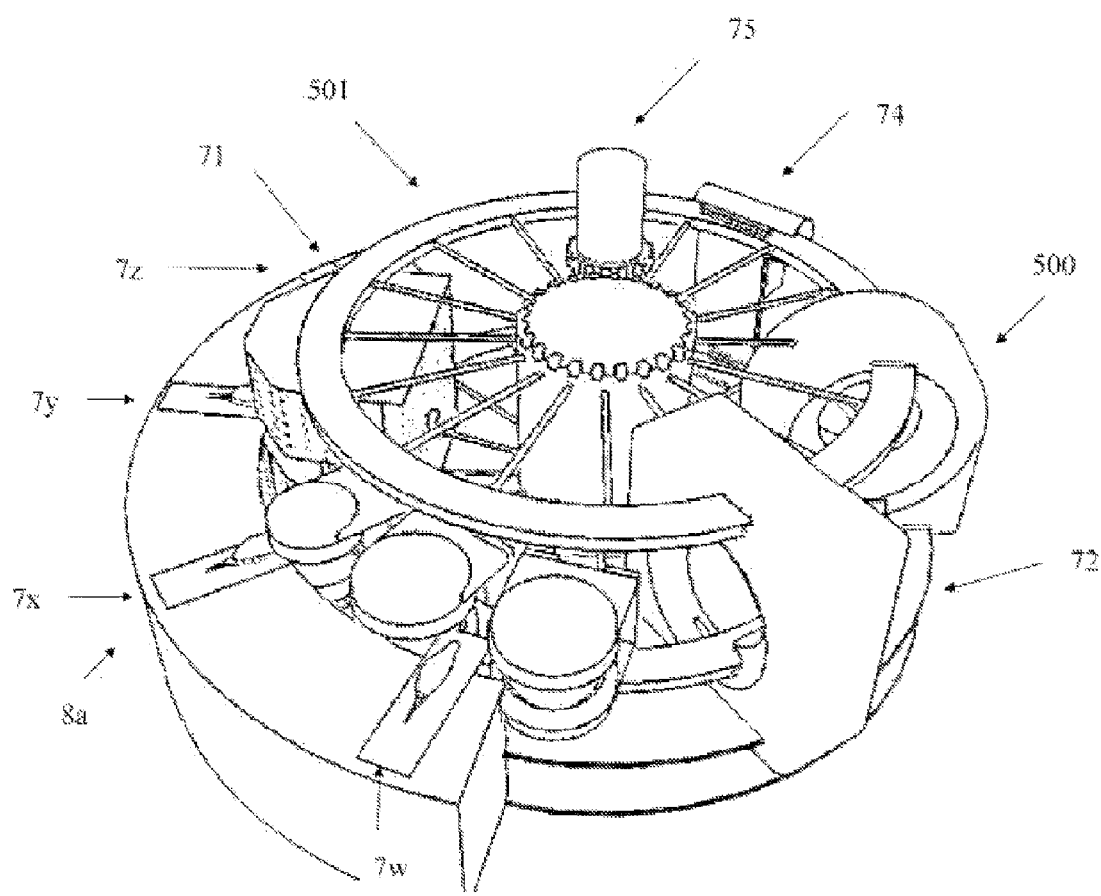
FIG. 8 is a perspective view of a measurement system according to a further embodiment of the present invention.

FIG. 8 is a perspective view of a measurement system 500 according to a further embodiment of the present invention. Measurement system 500 includes a stationary table 8*a*, RF coils 7*w*, 7*x*, 7*y* and 7*z*, a first rotating imaging assembly 71, a second rotating imaging assembly 72, a third rotating imaging assembly 73, a fourth rotating imaging assembly 74, a control unit 75 and a rotating mechanism 501 for rotating the imaging assemblies around the stationary table 8*a*. The rotating mechanism 501 may be configured from a motor, pulleys, belts, etc. and communicates with the control unit 75 in order to synchronize the imaging of the measurement objects. In other words, rotating mechanism 501 operates in a similar manner as the rotational drive mechanism 9, but instead of advancing rotating table 8 around the various stationary imaging assemblies, rotating mechanism 501 advances the rotating imaging assemblies around the stationary table 8a. In this case, since the measurement objects remain stationary, these objects feel no discomfort during measurement, thus creating a measurement system that is gentle to the measurement objects. According to a further embodiment of the present invention, the measurement objects and the imaging assemblies can both rotate for enhanced measurement capabilities.

The measurement device and measurement method of the present invention are useful as a device and method for obtaining images of measurement subjects using a variety of types of magnetic resonance, such as electron spin resonance, nuclear magnetic resonance, etc. In particular, the present invention is preferable as a way of eliminating the load imposed through stopping a measurement subject moving between multiple magnetic field generation devices.

The invention claimed is:

1. A measurement device, comprising:
    a first magnetic field generating device for generating a magnetic field of a set size;
    a second magnetic field generating device for generating a magnetic field of a size that differs from that of the magnetic field of the first magnetic field generating device;
    a rotating movement device for causing a measurement subject to pass in sequence through the magnetic fields of the first and second magnetic field generating devices by causing the measurement subject or the first and second magnetic field generating devices to move rotationally without stopping; and
    a measurement processing part that measures images of the measurement subject in different magnetic fields without stopping the measurement subject or the magnetic field generating devices while the measurement subject is or the magnetic field generating devices are being moved rotationally by the rotating movement device.

2. The measurement device according to claim 1, wherein one of the first and second magnetic field generating devices is for exciting and measuring nuclear magnetic resonance, and the other is for exciting and measuring electron spin resonance.

3. The measurement device according to claim 1, wherein the second magnetic field generating device generates a magnetic field larger than the magnetic field of the first magnetic field generating device.

4. The measurement device according to claim 1, wherein the first magnetic field generating device generates a magnetic field larger than the magnetic field of the second magnetic field generating device.

5. The measurement device according to claim 1, wherein the first or second magnetic field generating device is for exciting and measuring magnetic resonance.

6. A measurement method, comprising:
    causing a measurement subject to pass in sequence through the magnetic fields of a first magnetic field generating device that generates a magnetic field of a set size and a second magnetic field generating device that generates a magnetic field of a size that differs from that of the magnetic field of the first magnetic field generating device by causing the measurement subject or the first and second magnetic field generating devices to move rotationally without stopping; and
    measuring images of the measurement subject in different magnetic fields without stopping the measurement subject or the first and second magnetic field generating devices while the measurement subject is or the first and second magnetic field generating devices being moved rotationally by the rotating movement device.

7. The measurement method according to claim 6, further comprising:
    exciting and measuring nuclear magnetic resonance by either the first or the second magnetic field generating device; and
    exciting and measuring electron spin resonance by the other of the first or the second magnetic field generating device.

8. The measurement method according to claim 6, further comprising generating a magnetic field by the second magnetic field generating device larger than the magnetic field of the first magnetic field generating device.

9. The measurement method according to claim 6, further comprising generating a magnetic field by the first magnetic field generating device larger than the magnetic field of the second magnetic field generating device.

10. The measurement method according to claim 6, further comprising exciting and measuring magnetic resonance by either the first or the second magnetic field generating device.

* * * * *

UNITED STATES PATENT AND TRADEMARK OFFICE
CERTIFICATE OF CORRECTION

| | |
|---|---|
| PATENT NO. | : 8,532,740 B2 |
| APPLICATION NO. | : 13/002920 |
| DATED | : September 10, 2013 |
| INVENTOR(S) | : Ichikawa |

It is certified that error appears in the above-identified patent and that said Letters Patent is hereby corrected as shown below:

On the Title page, item [73]: delete "Kyushi University" insert --Kyushu University--.

Signed and Sealed this
Eighteenth Day of March, 2014

Michelle K. Lee
*Deputy Director of the United States Patent and Trademark Office*